(12) United States Patent
Belgrader (10) Patent No.: US 7,955,840 B2
(45) Date of Patent: Jun. 7, 2011

(54) THERMAL CYCLER FOR PCR INCLUDING TEMPERATURE CONTROL BLADDER

(75) Inventor: Phil Belgrader, Severna Park, MD (US)

(73) Assignee: Akonni Biosystems, Frederick, MD (US)

(*) Notice: Subject to any disclaimer, the term of this patent is extended or adjusted under 35 U.S.C. 154(b) by 334 days.

(21) Appl. No.: 11/843,843

(22) Filed: Aug. 23, 2007

(65) Prior Publication Data

US 2009/0053772 A1 Feb. 26, 2009

(51) Int. Cl.
*C12M 1/38* (2006.01)

(52) U.S. Cl. ............... 435/303.1; 435/91.2; 422/138

(58) Field of Classification Search .............. 165/104.11, 165/82, 83, 80.5, 111, 158, 165; 422/138, 422/131; 435/91.2, 303.1
See application file for complete search history.

(56) References Cited

U.S. PATENT DOCUMENTS

| | | | |
|---|---|---|---|
| 5,851,492 A * | 12/1998 | Blattner | 422/102 |
| 5,857,358 A * | 1/1999 | De Vries et al. | 65/106 |
| 6,086,679 A | 7/2000 | Lee | |
| 6,345,610 B1 | 2/2002 | Yang | |
| 6,734,398 B1 * | 5/2004 | Cecchi | 219/218 |
| 2003/0059490 A1 * | 3/2003 | Moore, Jr. | 425/2 |
| 2005/0226779 A1 * | 10/2005 | Oldham et al. | 422/99 |
| 2006/0246580 A1 | 11/2006 | Kim et al. | |

FOREIGN PATENT DOCUMENTS

JP 03111108 5/1991

OTHER PUBLICATIONS

Fluid—definition from Merriam-Webster dictionary online (www.m-w.com). Oct. 30, 2009.*

* cited by examiner

*Primary Examiner* — William H Beisner
*Assistant Examiner* — Michael Hobbs
(74) *Attorney, Agent, or Firm* — Andrews Kurth LLP (57) ABSTRACT

Methods and devices for performing chemical reactions under controlled temperatures are described. In one embodiment, the devices provided by the invention comprise a housing dimensioned to hold a reaction chamber disposed within an interior volume of the housing. The reaction chamber has thermally conductive interior and exterior surfaces defining an internal volume therein at a first temperature. The device also includes at least one thermally conductive temperature-control bladder disposed therein, which bladder is configured to receive a temperature-control substance at a second temperature into said bladder and expel said temperature-control substance from said bladder. The bladder is further configured such that upon receiving the temperature-control substance, the bladder expands to abut substantially at least a portion of said exterior surfaces of said reaction chamber to enable thermal exchange between said temperature-control substance the said internal volume of reaction chamber.

11 Claims, 7 Drawing Sheets

THERMAL CYCLER FOR PCR INCLUDING TEMPERATURE CONTROL BLADDER

1 BACKGROUND OF THE INVENTION

1.1 Field of the Invention

The invention relates to devices for performing chemical reactions, and in particular automated devices for performing polymerase chain reaction (PCR). Still more particularly, the present invention provides methods and apparatus for controlling reaction temperatures in an automated PCR device. The present invention has applications in the areas of analytical chemistry, molecular biology, and process chemistry.

1.2 The Related Art

Polymerase Chain Reaction (PCR) has become a mainstay of biochemical laboratories, and with good reason: this elegant method of replicating oligonucleotides using polymerase enzymes, such as Taq polymerase, has been a major factor in the explosion of biotechnological research and products. The process and its applications are well known those persons having ordinary skill in the art (Ausubel, Brent et al. 1992). In brief, PCR enables the rapid replication of oligonucleotides, in particular DNA, so that single copies of an oligonucleotide can be transformed into a significant concentration to enable further manipulation or analysis. The PCR procedure involves: transferring target oligonucleotide from a sample into a crude extract; adding an aqueous solution containing various enzymes, buffers, triphosphates (dNTPS), and complimentary oligonucleotide primers to the extract to form a reaction mixture; cycling the temperature of the reaction mixture between two or three temperatures (e.g., 90° C.-96° C., 37° C.- 65° C., and 72° C.) repeatedly to enable replication of the target oligonucleotides; and then detecting the amplified oligonucleotides. Intermediate steps, e.g., purification of reaction products and incorporation of surface-bending primers, also may be included. Each cycle doubles the number of target oligomer sequences. PCR techniques can amplify a single molecule of an oligonucleotide or oligoribonucleotide about $10^6$-to about $10^9$-fold.

Because genetic information can be used to establish the identities of individuals and the types of organisms, and because PCR is capable of creating analyzable quantities of genetic material from very small samples, many technologies exist to facilitate the application of PCR to analytical and forensic tasks. In particular, the use of PCR to identify unidentified bodies and criminals is widely used in law enforcement and the military. The application of PCR to national defense and homeland security is also an area of active biodefense development. Also, doctors and hospitals increasingly want access to portable PCR technology for use in care giving. Examples of such uses include:

Screening blood, saliva, or urine samples for multiple infectious diseases associated with upper respiratory, intestinal, or STD infections.

Determining if an infectious disease is resistant to antibiotics.

Determining if an infection is viral or bacterial.

Identifying an individual's susceptibility to an adverse drug reaction.

Diagnosing a cancer type (e.g., breast, prostate, ovarian, pancreatic).

Identifying an individual's predisposition to Alzheimer's disease.

These applications have created a heavy demand for automated PCR apparatuses that can process small sample concentrations on-site at remote locations to provide analytical data to investigators and medical workers.

As note above, a fundamental operation during the PCR process is thermal cycling, i.e., the raising and lowering of reaction temperatures to enable the amplication process, in which the temperature of the reaction mixture is driven between about 60° C. and about 95° C. as often as fifty or more times. A thermal cycle typically has four segments: heating the sample to a first temperature; maintaining the sample at the first temperature; cooling the sample to a lower temperature; and maintaining the temperature at the lower temperature. Conventional PCR instrumentation typically uses an aluminum block holding as many as ninety-six conical reaction tubes in which the sample and necessary reagents for amplication are contained. The block is heated and cooled during the PCR amplification process, often using either a Peltier heating/cooling apparatus, or a closed-loop liquid heating/cooling system in which flowing through channels machined into the aluminum block. However, the large mass of the aluminum block, and the conductivity of aluminum, limit the rates of heating and cooling to about 1° C. per second; so a fifty-cycle PCR amplification process takes at least about two hours.

Moreover, the cooling rate of the aluminum block is significantly lower than the heating rate. The asymmetry between the heating and cooling rates reduces the efficiency of the PCR process. For example, unwanted side reactions can occur at temperatures between the extremes creating unwanted DNA products, such as so-called "primer-dimers" and anomalous amplicons that consume reagents necessary for the desired PCR reaction. Other processes, e.g., ligand binding (organic or enzymatic) also suffer from unwanted side reactions under non-uniform temperatures that often degrade the analysis. For these reasons, optimization of the PCR process and similar biochemical reaction processes requires that the desired optimal reaction temperatures be reached as quickly as possible, spending minimal time at intermediate temperatures. Therefore the reaction vessels containing the reactants must be designed to optimize heating and cooling rates, to permit real time optical interrogation, and to accept various sample volumes.

One automated PCR system is the MATCI device disclosed in U.S. Pat. No. 5,589,136 (Northrup, Raymond P. Mariella et al. 1996), which describes a device that uses a modular approach to thermal cycling and analysis: Each reaction is performed in its own thermal cycling sleeve, and each sleeve has its own associated optical excitation source and fluorescence detector. The low thermal mass of the thermal cycling sleeve allows the MATCI device to realize extremely fast thermal cycling: samples can be heated at a rate of up to 30° C./sec. and cooled at rate as great as 5° C./sec. Two other commercially available systems, sold under the trade names GeneXpert (Cepheid, Sunnyvale, Calif.) and Razor (Idaho Technology, Inc.), use disposable fluidic cartridges, each containing an flexible reaction chamber that expands under pressure to make tight contact with a solid heater located in the instrument (Petersen, McMillan et al. 1999). The Razor uses a flexible fluidic pouch and actuators that move a reaction slug within the pouch; the reaction zone walls of the pouch make tight contact with two solid heaters. In both cases, the heater is a solid and the disposable cartridge or pouch contains one or more reaction zones, each with a thin, flexible wall that makes thermal contact with the heater. Still another technology, sold commercially under the trade names TruDiagnosis™ and TruArray™ by Akonni Biosystems (Fredericksburg, Md.), rapidly screen a sample for hundreds of disease markers at one time by using hundreds of molecular biosensors arrayed in a microarray the size of a fingernail. The samples are conveyed through the array using microfluidic channels. The Akonni technology can provide accurate diagnostic results in less than 30 minutes to support an informed and timely treatment decision.

Nevertheless current approaches to handling thermal cycling are limited, depending on flexibility in the disposable component to create satisfactory thermal contact with the instrument hardware, are needed. In particular, methods and apparatus that provide the desired cycling performance without reliance on special reaction chamber materials offer the promise of reduced cost and greater efficiency. The present invention meets these and other needs.

2 SUMMARY OF THE INVENTION

The present invention provides methods and apparatus for controlling the temperature of a container, such as a reaction vessel in which chemical reagents are combined to produce reaction products under controlled temperatures.

In a first aspect, the present invention provides a device for performing a chemical reaction. In one embodiment, the devices provided by the invention comprise a housing dimensioned to hold a reaction chamber disposed within an interior volume of the housing. The reaction chamber has thermally conductive interior and exterior surfaces defining an internal volume therein at a first temperature. The device also includes at least one thermally conductive temperature-control bladder disposed therein, which bladder is configured to receive a temperature-control substance at a second temperature into the bladder and expel the temperature-control substance from the bladder. The bladder is further configured such that upon receiving the temperature-control substance, the bladder expands to abut substantially at least a portion of the exterior surfaces of the reaction chamber to enable thermal exchange between the temperature-control substance and the internal volume of reaction chamber.

In some embodiments, the aforementioned thermal exchange between the temperature-control substance and the internal volume of the reaction chamber is effective to change the temperature of the internal volume of the reaction chamber from the first temperature to a third temperature at least intermediate the first and second temperature. In more specific embodiments, thermal exchange between the temperature-control substance and the internal volume of the reaction chamber is effective to change the temperature of a substance contained within the reaction chamber from the first temperature to a third temperature at least intermediate the first and second temperatures.

In a second aspect, the present invention provides a method for changing the temperature of the internal volume of a container. The method of the invention comprises providing a housing dimensioned to hold a reaction chamber disposed within an interior volume of the housing, the reaction chamber having thermally conductive interior and exterior surfaces defining an internal volume at a first temperature. The housing further includes at least one thermally conductive temperature-control bladder disposed within the housing which is configured to receive a temperature-control substance at a second temperature into the bladder and expel the temperature-control substance from the bladder. The bladder is further configured such that upon receiving the temperature-control substance the bladder expands to abut substantially at least a portion of the exterior surfaces of the reaction chamber to enable thermal exchange between the temperature-control substance and the internal volume of reaction chamber. The method further includes introducing the temperature-control substance under conditions effective to cause an expansion of the bladder to bring the bladder into substantially abutting the at least a portion of the exterior surfaces of the reaction chamber to enable thermal exchange between the temperature-control substance and the internal volume of reaction chamber.

In some embodiments, the aforementioned thermal exchange between the temperature-control substance and the internal volume of the reaction chamber is effective to change the temperature of the internal volume of the reaction chamber from the first temperature to a third temperature at least intermediate the first and second temperature. In more specific embodiments, thermal exchange between the temperature-control substance and the internal volume of the reaction chamber is effective to change the temperature of a substance contained within the reaction chamber from the first temperature to a third temperature at least intermediate the first and second temperatures.

In other embodiments, the method includes introducing a substance into the internal volume of the reaction chamber. Still other embodiments, include maintaining the expansion of the bladder for a period sufficient to change the temperature of the substance to a third temperature intermediate the first temperature and the second temperature. In yet other embodiments, third temperature is substantially equal to the second temperature. In still more embodiments, the substance comprises a mixture of PCR reactants, and the third temperature is effective to induce a PCR reaction.

In another aspect, the present invention provides a device for performing a chemical reaction, comprising a reaction chamber having thermally conductive interior and exterior surfaces defining an internal volume within the reaction chamber at a first temperature. The device also includes at least one thermally conductive temperature-control bladder disposed proximal to the reaction chamber, the bladder being configured to receive a temperature-control substance at a second temperature into the bladder and expel the temperature-control substance from the bladder; and the bladder being further configured such that upon receiving the temperature-control substance the bladder expands to abut substantially at least a portion of the exterior surfaces of the reaction chamber to enable thermal exchange between the temperature-control substance and the internal volume of reaction chamber.

In yet another aspect, the invention provides a method for changing the temperature of the internal volume of a container, comprising providing a reaction chamber having thermally conductive interior and exterior surfaces defining an internal volume within the reaction chamber at a first temperature. Providing also at least one thermally conductive temperature-control bladder proximal to the reaction chamber, which is configured to receive a temperature-control substance at a second temperature into the bladder and expel the temperature-control substance from the bladder. The bladder is further configured such that upon receiving the temperature-control substance the bladder expands to abut substantially at least a portion of the exterior surfaces of the reaction chamber to enable thermal exchange between the temperature-control substance and the internal volume of reaction chamber. The method further includes introducing the temperature-control substance under conditions effective to cause an expansion of the bladder to bring the bladder into substantially abutting the at least a portion of the exterior surfaces of the reaction chamber to enable thermal exchange between the temperature-control substance and the internal volume of reaction chamber.

These and other aspects and advantages will become apparent when the Description below is read in conjunction with the accompanying Drawings.

3 BRIEF DESCRIPTION OF THE DRAWINGS

FIGS. 1A, 1B, and 1C illustrate one embodiment of a device in accordance with the present invention.

4 DESCRIPTION OF SOME EMBODIMENTS OF THE INVENTION

Figure 1A:
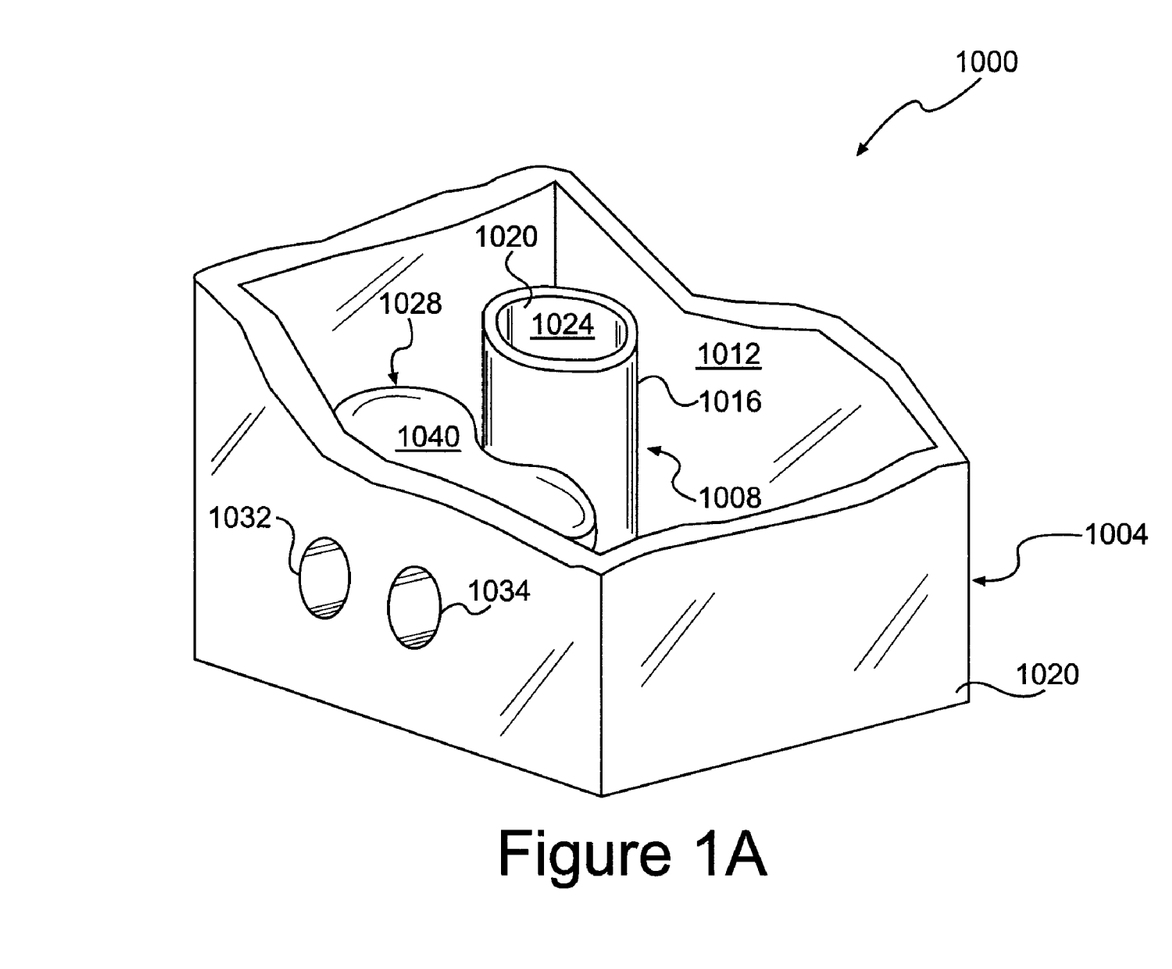
FIG. 1A is a partial cut-away view of such a device.

In a first aspect, the present invention provides a device for controlling the temperature of a defined volume. In one embodiment, the defined volume is a reaction chamber configured for holding chemical reactants and performing a chemical reaction therein at controlled temperatures. In a more particular one embodiment, shown in FIG. 1A (1000), the device provided by the invention includes a housing (1004). The housing can be constructed from materials and designs well known to persons having ordinary skill in the art. Examples of such materials include, without limitation, plastics, metals, ceramics, composites, and the like. Examples of housing embodiments include those in which the housing is of lightweight construction (e.g., thin plastic), hermetically sealed (e.g., for containing harmful substances, such as hazardous chemical and biological substances), or capable of holding a vacuum in the interior space. Thus, in some embodiments, the housing includes means for reducing the pressure (i.e., inducing a vacuum) within the housing (i.e., within interior space 1012); and in other embodiments, the housing includes one or more inlets or ports for adding reagents. The housing may also include sensors, reactant supplies, and other components as will be familiar to those persons having ordinary skill in the art. Still more designs and specifications will be familiar to persons having ordinary skill in the art. The particular choices of materials and design will depend on the anticipated function and operating conditions of the device as will be understood by persons having ordinary skill in the art.

Figure 1B:
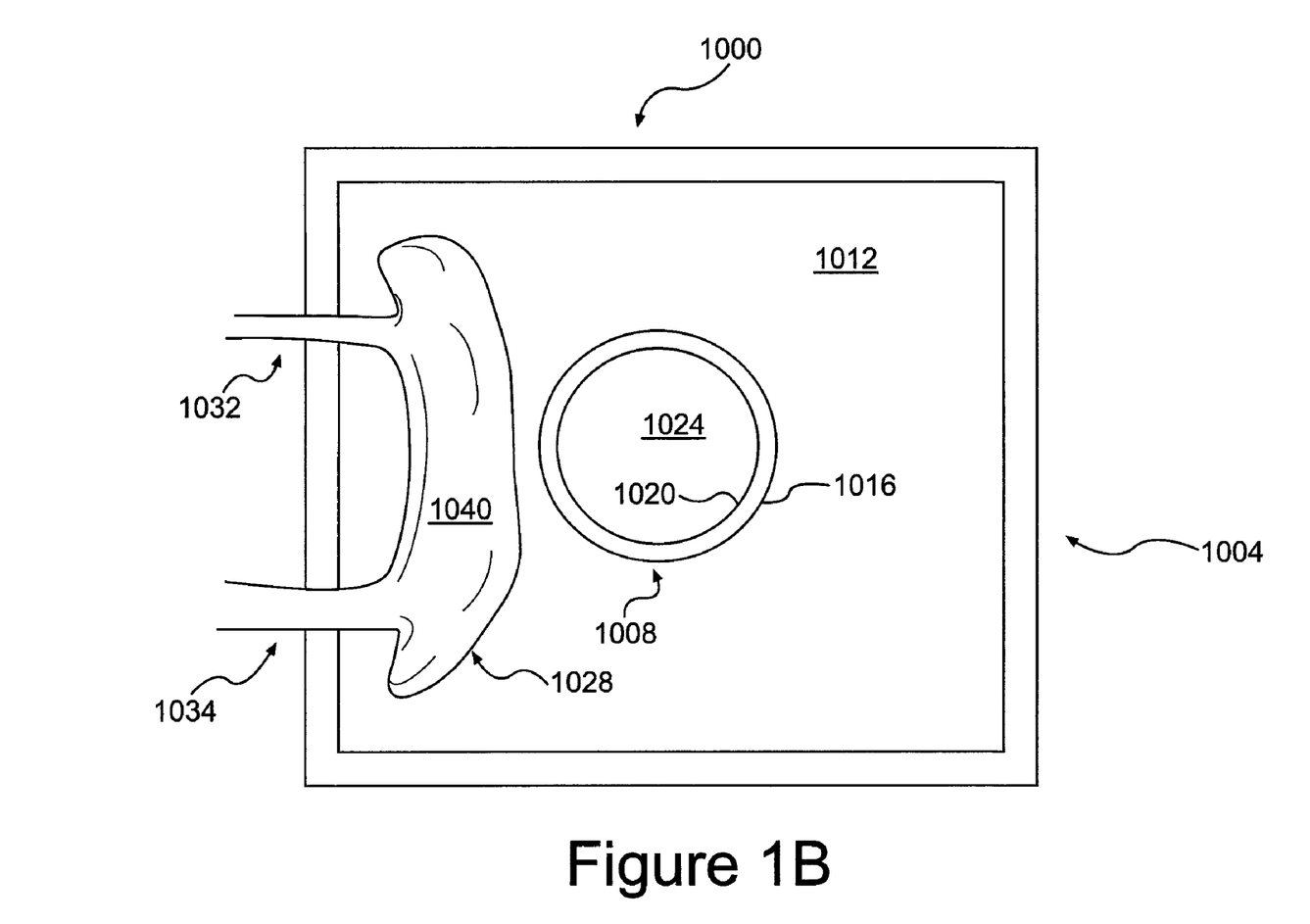
FIG. 1B is a cut-away top view of the interior of such a device, with the bladder in a substantially deflated state.
Figure 1C:
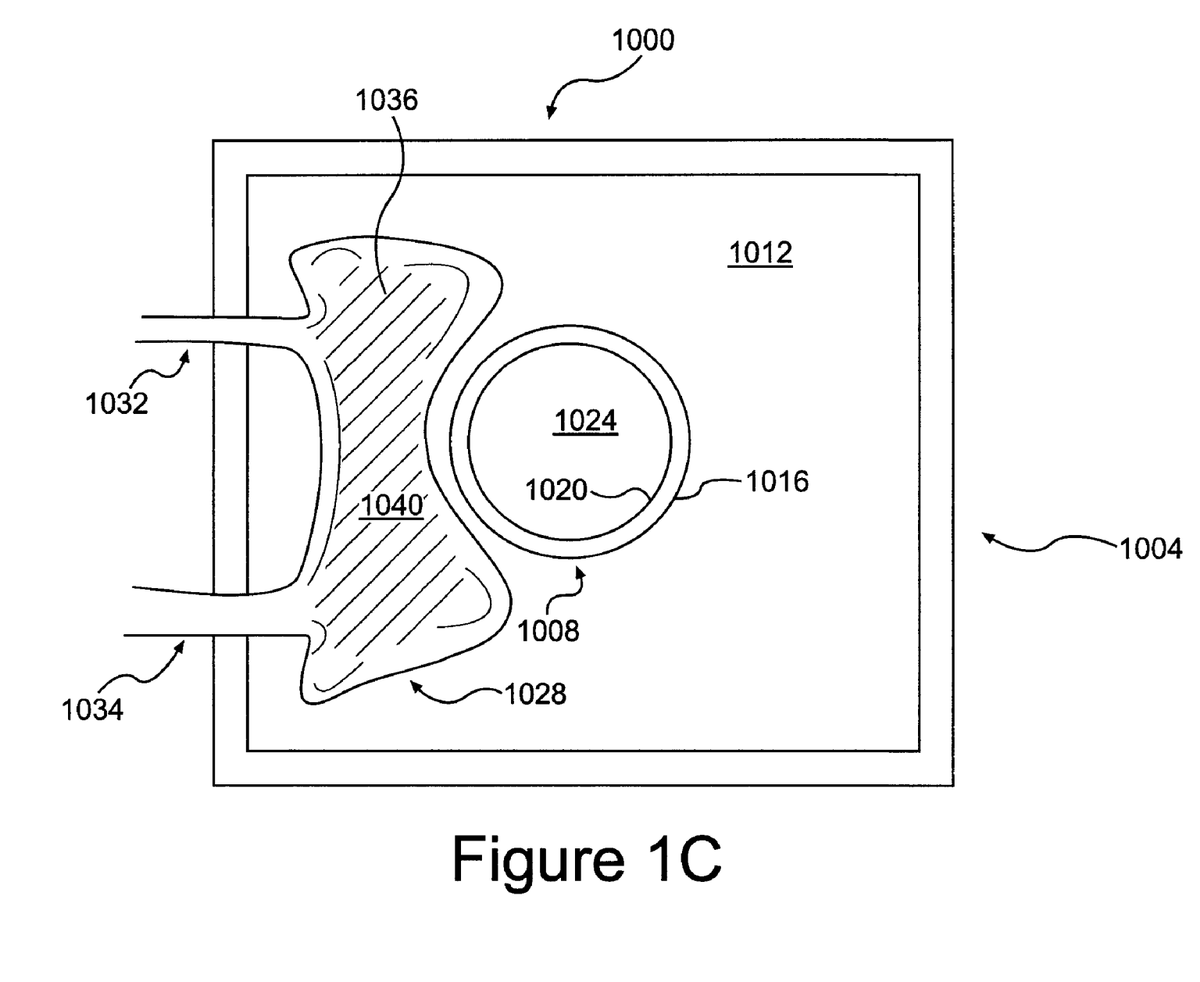
FIG. 1C is a cut-away top view of the interior of such a device, with the bladder in a substantially inflated state to provide thermal contact with a reaction vessel.

The device (1000) further comprises a reaction chamber (1008) arranged within the interior space of the housing (1012). The reaction chamber includes a thermally conductive outer wall (1016) and a thermally conductive inner wall (1020) defining an internal volume within the reaction chamber (1024) as shown in FIGS. 1B and 1C. The reaction chamber can be constructed from materials and designs well known to persons having ordinary skill in the art. Examples of such materials include, without limitation, plastics, metals, ceramics, composites, and the like. Exemplary embodiments include those in which the reaction chamber is of lightweight construction (e.g., thin plastic), hermetically sealed (e.g., for containing harmful substances, such as hazardous chemical and biological substances), or capable of holding a vacuum. In some embodiments, the reaction chamber is designed to hold a single mixture of materials; and, in more particular embodiments, includes a cap or other seal to create a closed system. In other embodiments, the reaction chamber has a substantially tubular design through which mixtures of materials travel in defined and disjoint volumes, commonly referred to as "slugs" (see FIG. 2). Still more designs and specifications will be familiar to persons having ordinary skill in the art. For example, the reaction chamber may include one or more inlets or ports for adding reagents or removing reaction products, internal sensors, and windows for external sensors. The particular choices of materials and design will depend on the anticipated function and operating conditions of the device as will be understood by persons having ordinary skill in the art.

Returning to FIG. 1A, also disposed within the interior of the housing are one or more temperature-control pouches or temperature-control bladders (1028) that are disposed proximal to the reaction chamber and configured to control, mediate, or otherwise modify the temperature of the internal volume of the reaction chamber (1024). The pouch or bladder is composed of a material having suitable mechanical and thermal properties, as will be understood by persons having ordinary skill in the art. Examples of suitable materials include, but are not limited to: silicone, latex, mylar, polyurethane, polypropylene, and polyethylene. In other embodiments the above-described bladders comprise a gel material healed by a heat source such as a resistive or peltier heater. Each bladder is configured to accept a temperature control material (show at 1036 in FIG. 1 C), such as a liquid or gas at a controlled temperature, that is introduced into the hollow space (1040, see FIG. 1B) of bladder 1028, e.g., through inlets and outlets such as shown at 1032 and 1034, respectively, in FIG. 1A. The temperature-control substance can be stored in a reservoir or other repository from which the temperature of the temperature-control substance can be modified by an operator. In another embodiment, withdrawal of the temperature-control substance from the bladder after introduction is effective to return the bladder to the above-described disengaged state by reducing, and optionally preventing, the above-described thermal exchange. Thus, by introducing and withdrawing the temperature-control substance, the temperature of the internal volume can be modulated in a controlled fashion. In one embodiment, the temperature control material is water, and the bladder is connected to a water circuit that can provide water at a desired temperature to the bladder. Suitable temperature-control materials, means for regulating the temperature of such materials, and means for introducing such materials to, and withdrawing them from, the pouch or bladder is also familiar to those having ordinary skill in the art.

In one embodiment, the introduction of the temperature-control material into the bladder is effective to induce expansion of the bladder from a substantially non-abutting disengaged position (see FIG. 1B) to an engaged position in which the bladder abuts substantially at least a portion of the outer wall (1016) of the reaction chamber (see FIG. 1C), providing thereby thermal exchange between the temperature control material and the internal volume of the reaction chamber (1024) through the walls of the bladder and reaction chamber. Thus, in one embodiment, the internal volume of the reaction chamber is at a first temperature, the temperature-control material is at a second temperature, and the thermal contact between the two is effective to change the temperature of the internal volume of the reaction chamber from the first temperature to a third temperature that is at least intermediate the first and second temperature. In a more specific embodiment, the third temperature is substantially equal to the second temperature. In more specific embodiments, the internal volume of the reaction chamber contains a substance, such as a mixture of reactants or an analyte, is at a temperature substantially equal to the first temperature prior to the above-described thermal exchange and brought to a temperature substantially equal to the third temperature following such thermal exchange. In a still more particular embodiment in which the internal volume contains a substance, the third temperature is substantially equal to the second temperature.

Figure 2:
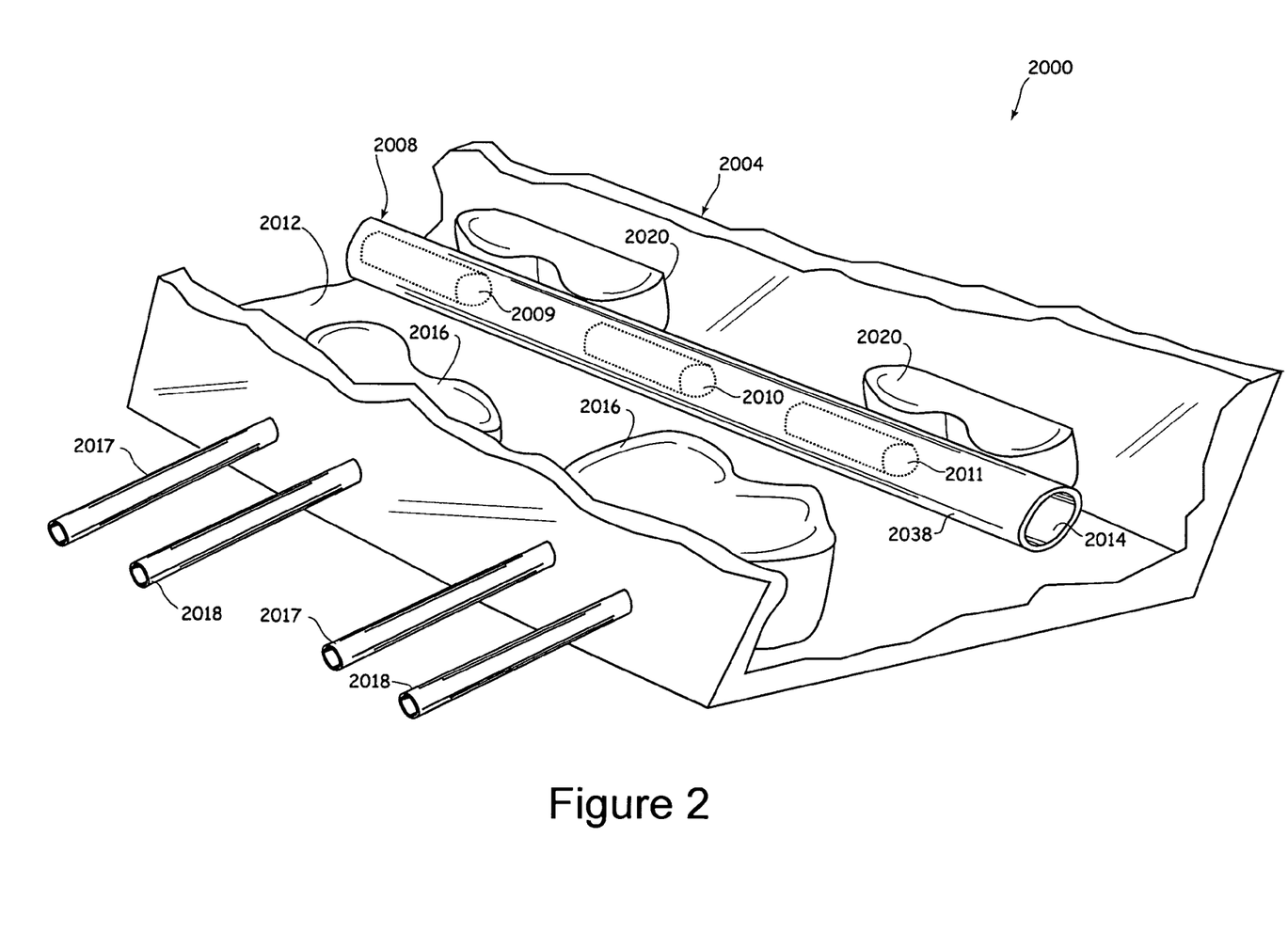
FIG. 2 is a partial cut-away view of another embodiment of a device in accordance with the present invention that comprises multiple sets of bladders.

One, two, or more pouches or bladders can be arranged proximal to the reaction chamber by analogy to the descriptions provided herein, as illustrated in FIG. 2 at (2000). There, a housing (2004), such as described above, includes a reaction chamber (2008) that holds a series of slugs of reactants (2009, 2010, 2011), which are transported through the reaction chamber and in contact with the interior surface of the reaction chamber (2014). Proximally adjacent the reaction chamber are two sets of temperature-control pouches or bladders arrayed in pairs on opposing sides of the reaction chamber (2016, 2020), connected with inlets (2017) and outlets (2018), which operate as described above. In one embodiment, the slugs are transported through the internal volume of the reaction chamber and paused at defined locations whereupon one or more of the bladders engages the outer wall of the reaction chamber (2038) to modulate the temperature of the slug by thermal exchange as described above. The bladders may be filled with a temperature-control substance at single temperature, to provide substantially equal heat exchange by all bladders, or different bladders can hold temperature-control substances at different temperatures. In some embodiments, different bladders can even hold different temperature-control substances to provide different thermal exchange properties.

In another embodiment, the substance (which may be in the form of one or more slugs) contained in the internal volume of the reaction chamber is a mixture of reagents for performing a PCR reaction. In a more specific embodiment, the reaction chamber is a disposable analytical cartridge, such as available commercially, that holds the PCR reagents. In a more specific embodiment, the reaction cartridge is inserted into the housing and the temperature-control substance is introduced into bladders, which thereby expand and told the cartridge and heat the reactants for a pre-determined time. At a chosen moment, the temperature-control substance is withdrawn, and the bladders deflate to reduce or check further thermal exchange. This disengaged configuration can be maintained for a determined period, after which the bladders are again engorged to bring the reactants back to the earlier temperature or, optionally, a different temperature. Successive phases of engagement and disengagement, using temperature-control substances at a constant or varying temperature, can be performed to perform reactions at defined time-temperature cycles. Such thermal cycling will be familiar to persons having ordinary skill in the art.

One particular embodiment includes a single, static reaction chamber containing reactants for a PCR amplification of an oligomer. One or more bladder(s) is (are) brought into contact with the reaction chamber, each of which bladders contain the same circulating temperature-control substance. A valve diverts the temperature-control substance from two or more reservoirs of temperature-control substance that are at different temperatures, so that the PCR mixture can be brought to different temperatures by exchanging the temperature-control fluids in the bladders. During the thermal cycling, a temperature-control substance at 95° C. is circulated into the bladders to heat, and thereby denature the oligomers, and then withdrawn. Next, a temperature-control substance at 60° C. is circulated into the bladders to enable the primers to hybridize and extend to generate PCR amplication product. This sequence is performed for between about 30 and about 50 cycles.

In another embodiment, two bladders are brought into contact with a single reaction chamber, wherein each bladder contains a circulating temperature-control substance at a different temperature (e.g., one at 95° C. and the other at 60° C.). Expansion and contraction of the bladders as described above determines which bladder makes contact with the reaction chamber or channel. In still another embodiment, a single reaction chamber has two or more reaction zones in a single channel. Each zone interfaces with a different bladder; and each bladder is at a different temperature. e.g., 95° C. and 60° C. respectively. The reaction slug is moved hack and forth between temperature zones to produce the desired thermal cycling. (See FIG. 2, described above.)

In other embodiments, one or more of the above-described bladders is replaced by a resistive heater, a peltier, or temperature-controlled air, either singly or in combination.

In still other embodiments, the above-described reaction chamber is replaced with a microarray having immobilized primers at each microarray spot.

5 EXAMPLES

Figure 3:
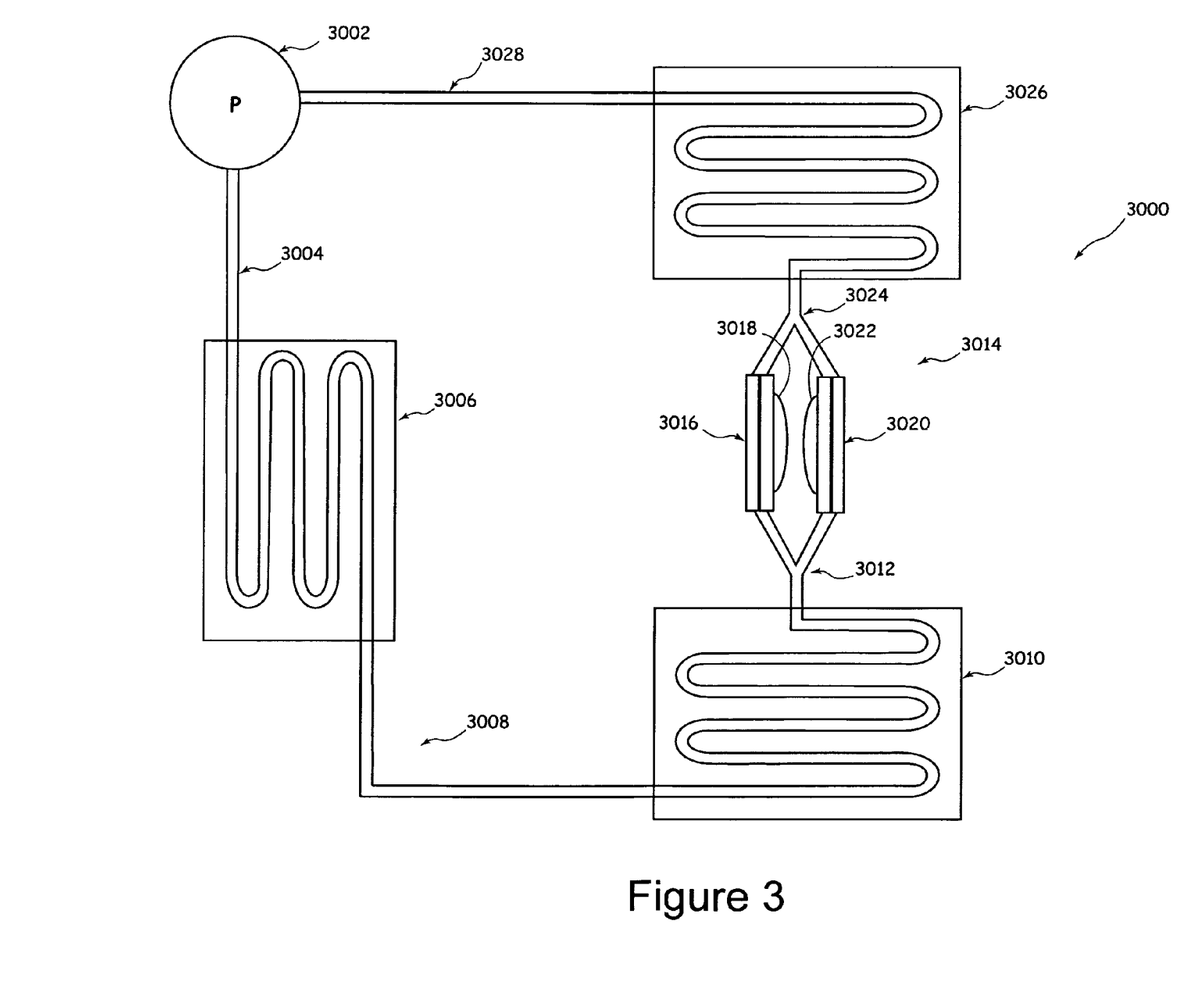
FIG. 3 is a schematic illustrating one exemplary embodiment of the invention.

FIG. 3 provides a schematic illustration of one embodiment of the invention (3000). A pump (3002) of standard construction as will be understood by those having ordinary skill in the art, was connected to and outlet line (3004) that carried water through a heat exchanger (3006) made using materials known to persons having ordinary skill in the art. The outlet line from the heat exchanger (3008) carried the water to a first heater (3010) configured to heat the water to about 95° C. The water was then passed through a branch (3012) that splits the path into the bladder unit (3014), which includes a first bladder support (3016) coupled to a first bladder (3018) in a substantially opposing arrangement to a second bladder support (3020) coupled to a second bladder (3022). Water exiting the bladder unit (3014) is combined back into a single path by a second branch (3024) and then passes into a second heater (3026) configured to heat the water to about 65° C. A return path (3028) brings the water back to the pump. Each of the bladders has a capacity of five milliliters (ml), each of the heaters can hold 22 ml, and the heat exchanger can hold between five ml and 22 ml. By cycling the water reversibly between each of the heaters and heat exchanger, the bladders can cycle the temperature of a sample held in the bladder unit between a nominal starting temperature, 65° C., and 95° C.

Figure 4:
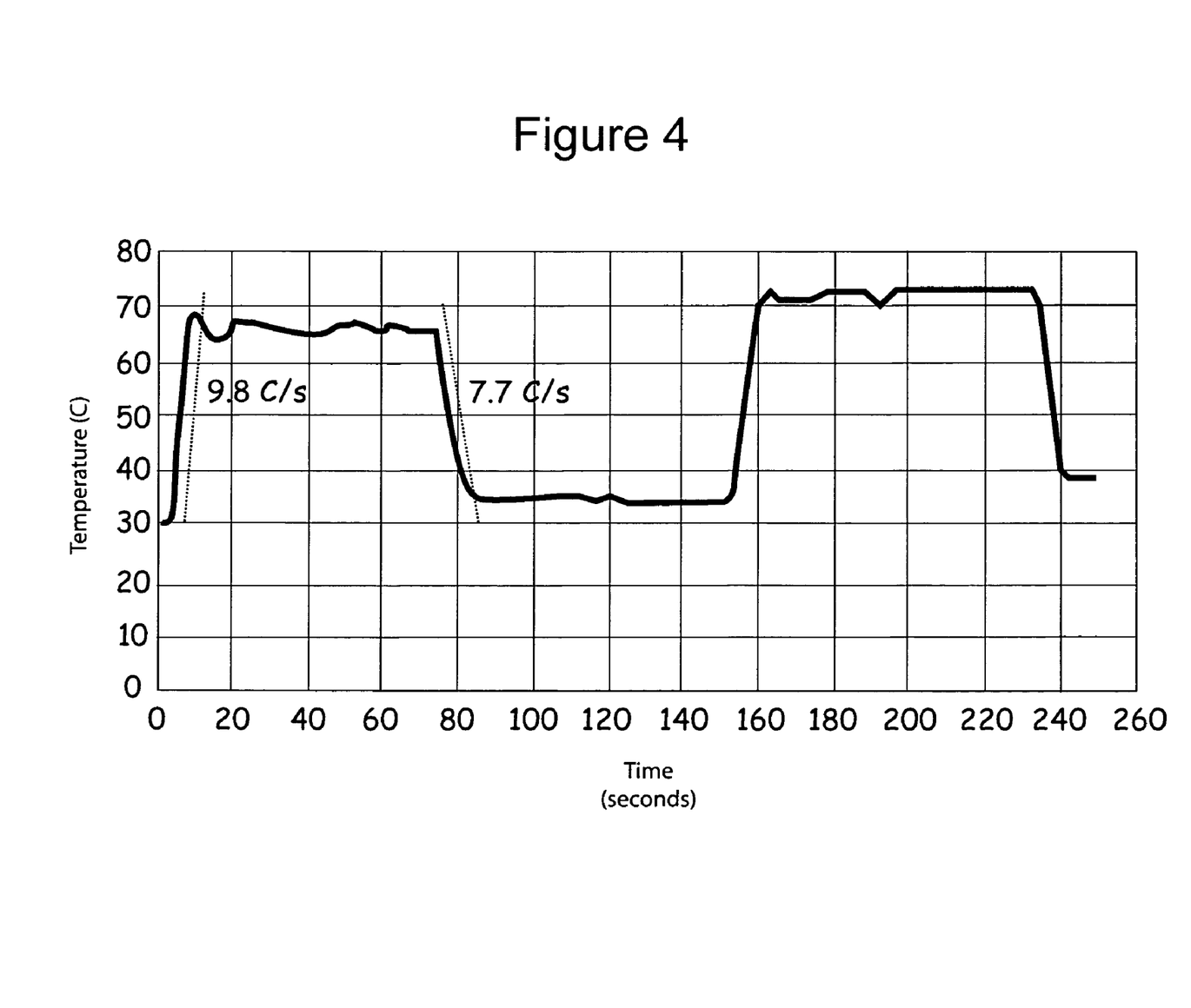
FIG. 4 is a graph showing heating and cooling as a function of time for the embodiment illustrated in FIG. 3.

The performance of the device described with reference to FIG. 3 is shown in FIG. 4. There, water at an initial temperature of about 65° C. in about three to four seconds (i.e., heated at a rate of about 9.8° C./s), held at that temperature for about one minute, cooled back to the starting temperature in about five seconds (i.e., at a rate of about 77° C./s), then heated to about 95° C. in about 10 seconds, held at that temperature for about 75 seconds-80 seconds, and then cooled to about 40° C.

Figure 5:
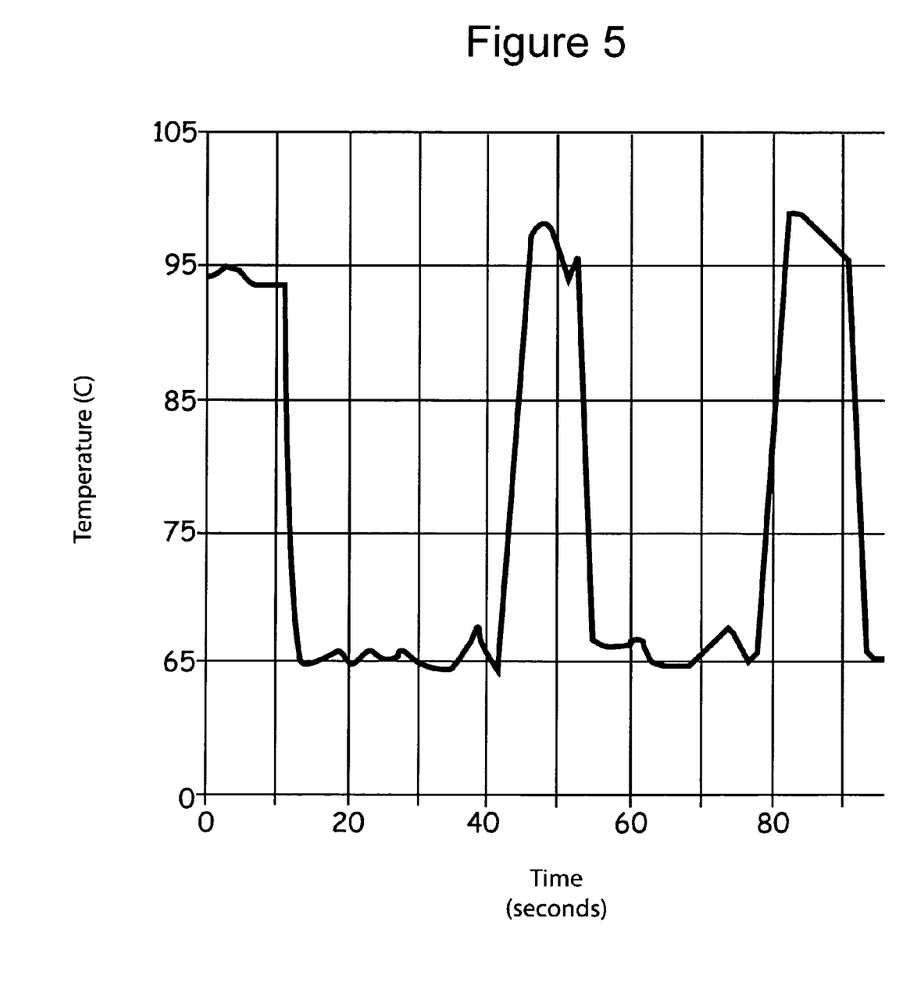
FIG. 5 is a graph showing heating and cooling as a function of time for the embodiment illustrated in FIG. 3.

A second example of the performance of the device described with reference to FIG. 3 is shown in FIG. 5. There, water in a reaction chamber was held between a pair of bladders is heated to 95° C. and held at the temperature for at least ten seconds, then cooled back to about 65° C. in about two seconds (i.e., at a rate of about 15° C./s), held at the temperature for about 25 seconds, heated to about 95° C. in about three seconds (i.e., at a rate of about 10° C./s), held at that temperature for about one second, and then cooled again to about 65° C. in about three seconds, held at that temperature for about 25 seconds. The heating and cooling cycle was repeated as described and shown.

In an exemplary embodiment of a method for operation of the above-described invention, an operator places a sample for PCR amplification in a disposable cartridge reaction chamber. The cartridge is loaded into the instrument and aligned with the relaxed, i.e., disengaged, bladders. Instrument operation is initiated, and the bladders are charged with circulating temperature-control fluid. The fluid reservoirs begin heating to reach operating temperature while the sample is being processed. The processed sample is nixed with PCR reagents on the cartridge, and the mixture is moved to the PCR reaction chamber. Thermal cycling is performed in the cartridge reaction chamber by valve control of two reservoirs of fluids at different temperatures (e.g., at 95° C. and 60° C.). The thermal cycling continues for between about 30 and about 45 cycles. The reaction mixture containing the desired PCR product is then moved to a microarray component. When the instrument's operation is completed, the bladder is drained, thereby relieving the pressure to no longer make contact with the cartridge. The cartridge is then removed from the instrument.

6 CONCLUSION

Thus it will be seen that the present invention provides important apparatuses and methods for controlling the temperature in a reaction chamber, and especially, a reaction chamber used to perform PCR reactions. Exemplary advantages provided by the apparatuses and methods described herein include, but are not limited to the following:

Bladders allow simplified fluidic-based heat transfer to a disposable cartridge for efficient and reproducible thermal cycling in the cartridge.

Deflated bladders allow easy insertion of disposable cartridges containing a reaction chamber.

Use of bladder avoids liquid interconnects to the disposable cartridge for fluid circulation.

Although various specific embodiments and examples have been described herein, those having ordinary skill in the art will understand that many different implementations of the invention can be achieved without departing from the spirit or scope of this disclosure. For example, encryption and decryption can be performed using a single software module or more than two software modules. The modules described herein can be implemented using a variety of techniques and can be part of the operating system as well as plug-ins. Still other variations will be clear to those having ordinary skill in the art.

7 BIBLIOGRAPHY

The following reference are each incorporated in their entireties and for all purposes.

Ausubel, F. M., Brent, R., et al., Eds. (1992). *Short Protocols in Molecular Biology.* Current Protocols in Molecular Biology. New York, John Wiley & Sons.
Northrup, M. A., Raymond P. Mariella, J., et al. (1996). *Silicon-Based Sleeve Devices for Chemical Reactions.* U.S. Pat. No. 5,589,136.
Petersen, K. E., McMillan, W. A., et al. (1999). *Reaction Vessel for Heat Exchanging Chemical Processes.* U.S. Pat. No. 5,958,349.

What is claimed:

1. A device for performing a polymerase chain reaction (PCR), comprising:
    a first heater for heating a temperature-control substance to a first temperature;
    a second heater for heating said temperature-control substance to a second temperature;
    a pump located in between and connected in series with said first heater and said second heater; and
    a bladder unit comprising a pair of bladders, each bladder is coupled to a bladder support and is connected to said first and second heaters via different ports,
    wherein said pair of bladders are inflatable with said temperature-control substance that controls the temperature of said pair of bladders, wherein said pair of bladders are positioned in a substantially opposing arrangement with a space in between such that both bladders, when inflated, are capable of contacting a reaction chamber placed in said space, and
    wherein said pump introduces said temperature-control substance into said pair of bladders at said first temperature and said second temperature alternatively with a regular interval to enable the PCR.

2. The device of claim 1, wherein said temperature-control substance is a liquid.

3. The device of claim 2, wherein said liquid is water.

4. The device of claim 1, wherein said pair of bladders are made from a material selected from the group consisting of silicone, latex, mylar, polyurethane, polypropylene and polyethylene.

5. The device of claim 1, wherein said first heater is in fluid communication with said pair of bladders through a first branch connection.

6. The device of claim 5, wherein said second heater is in fluid communication with said pair of bladders through a second branch connection.

7. A heating device for performing a polymerase chain reaction (PCR), comprising:
    a first bladder;
    a second bladder positioned in a substantially opposing arrangement with said first bladder;
    a first heater connected to said first and said second bladders via a first port on each bladder;
    a second heater connected to said first and said second bladders via a second port on each bladder;
    a heat exchanger located between said first and second heaters and connected in series with said first and said second heaters; and
    a pump located between and connected in series with said first heater and heat exchanger,
    wherein said first and second bladders are inflatable with a temperature-control substance that controls the temperature of said first and second bladders.

8. The heating device of claim 7, wherein said temperature-control substance is a liquid.

9. The heating device of claim 8, wherein said liquid is water.

10. The heating device of claim 7, wherein said first and second bladders are made from a material selected from the group consisting of silicone, latex, mylar, polyurethane, polypropylene and polyethylene.

11. The heating device of claim 7, wherein said pump is capable of cycling said temperature-control substance reversibly between each of said first and second heaters.

* * * * *